United States Patent [19]
Matsuura et al.

[11] Patent Number: 5,202,154
[45] Date of Patent: Apr. 13, 1993

[54] METHOD OF PRODUCING THICK-FILM GAS SENSOR ELEMENT HAVING IMPROVED STABILITY

[75] Inventors: Toshitaka Matsuura; Keizo Furusaki; Mineji Nasu; Akio Takami, all of Aichi, Japan

[73] Assignee: NGK Spark Plug Co., Ltd., Nagoya, Japan

[21] Appl. No.: 565,994

[22] Filed: Aug. 13, 1990

Related U.S. Application Data

[63] Continuation-in-part of Ser. No. 394,825, Aug. 17, 1989, abandoned.

[30] Foreign Application Priority Data

Sep. 19, 1988 [JP] Japan .................. 63-234633

[51] Int. Cl.$^5$ .................................. C23C 26/00
[52] U.S. Cl. ........................ 427/125; 427/126.3; 427/376.2
[58] Field of Search ................ 427/125, 126.3, 376.2

[56] References Cited

U.S. PATENT DOCUMENTS

| | | | |
|---|---|---|---|
| 4,234,367 | 11/1980 | Herron | 427/96 |
| 4,551,357 | 11/1985 | Takeuchi | 427/96 |
| 4,627,160 | 12/1986 | Herron | 427/96 |
| 4,720,394 | 1/1988 | Kojima | 427/102 |
| 4,857,275 | 8/1989 | Furnsaki | 427/343 |
| 4,965,092 | 10/1990 | Hayduk | 427/96 |

FOREIGN PATENT DOCUMENTS 93949 5/1985 Japan .
5165 1/1987 Japan .
231255 9/1988 Japan .

OTHER PUBLICATIONS

English translation of Japanese Patent 60-93949.
English translation of Japanese Patent 63-231255.
English translation of Japanese Patent 62-5165.

*Primary Examiner*—Shrive Beck
*Assistant Examiner*—Vi Duong Dang
*Attorney, Agent, or Firm*—Foley & Lardner

[57] ABSTRACT

The invention relates to a method of producing a gas sensor element having a porous film formed by a thick-film technique on a ceramic substrate surface so as to cover selected portions of electrode films precedingly formed on the substrate surface. The electrode material is a noble metal such as platinum. Both the electrode films and the gas sensitive porous thick-film are formed by known methods. To improve the contact between the gas sensitive porous thick-film and the electrode films both mechanically and electrically and stabilize the internal resistance of the sensor element by depositing a noble metal such as platinum at the interface between the porous thick-film and each electrode film, the porous thick-film is impregnated with a solution of a noble metal compound such as chloroplatinic acid and thereafter maintained in a reducing gas atmosphere having a controlled humidity in the range from 5 to 90% (relative humidity) at a temperature in the range from 10° C. to 135° C.

15 Claims, 5 Drawing Sheets

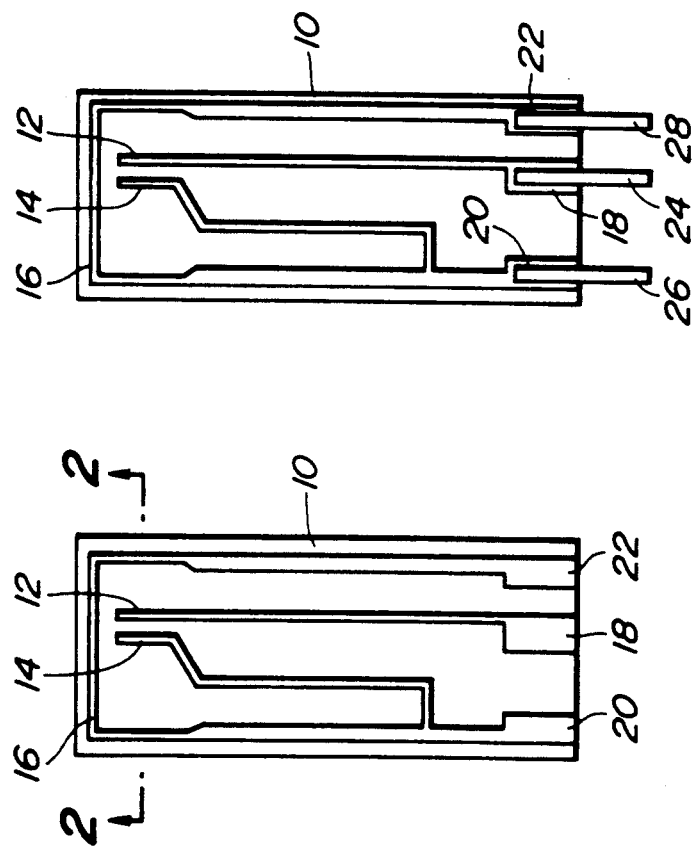

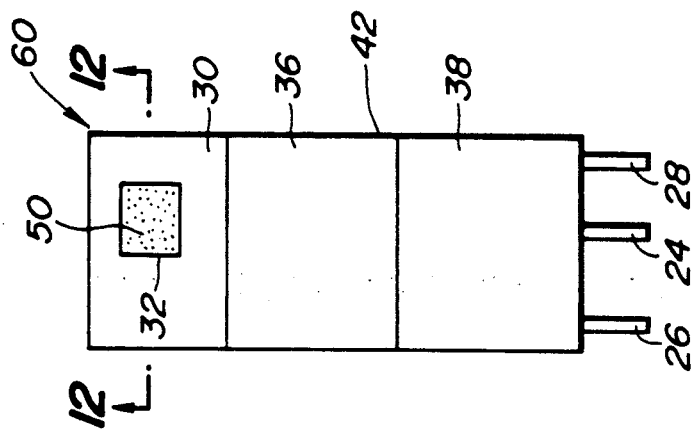
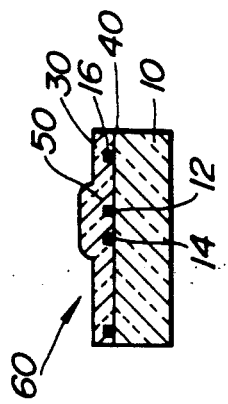
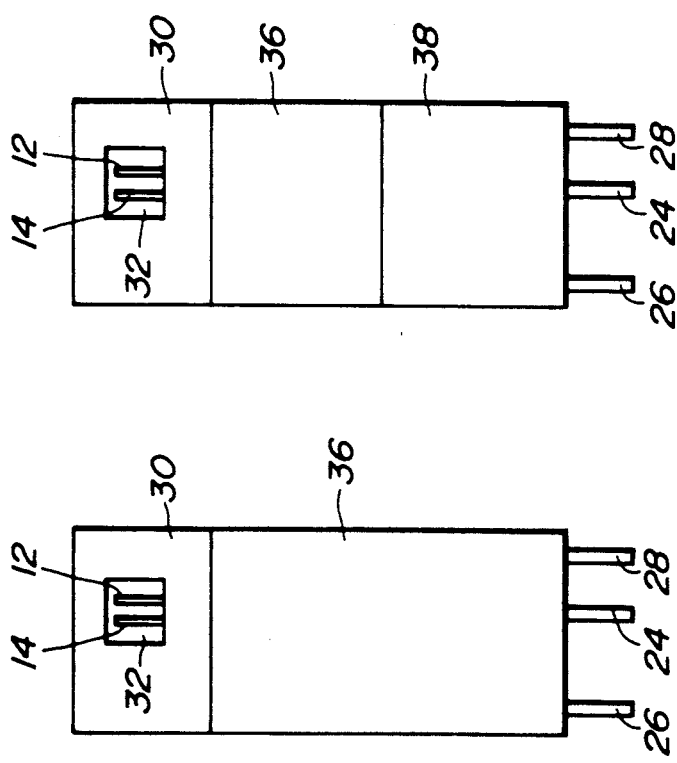
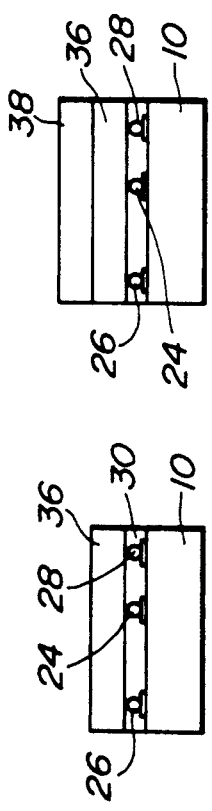

METHOD OF PRODUCING THICK-FILM GAS SENSOR ELEMENT HAVING IMPROVED STABILITY

This is a continuation-in-part of application Ser. No. 07/394,825, filed Aug. 17, 1989, now abandoned.

BACKGROUND OF THE INVENTION

This invention relates to a method of producing a gas sensor element having a porous film of a gas sensitive material formed by a thick film technique on a ceramic substrate so as to cover electrode films precedingly formed on the substrate, the method including steps for improving the strength and stability of the contact between the gas sensitive thick film and the electrode films.

In gas sensor elements of the aforementioned type, viz. thick film gas sensor elements, usually the gas sensitive thick film is formed on a flat and smooth surface of a ceramic substrate so as to make contact with both the substrate surface and the precedingly formed electrode films. A problem about this construction is that the thick film is liable to partially peel from the substrate surface during practical use of the gas sensor due to a difference between the thermal expansion coefficients of the thick film and the ceramic substrate. If the contact of the gas sensitive thick film with the electrode films is not good the internal resistance of the gas sensor element increases during operation of the sensor element, which causes lowering of the sensor output and adversely influences the accuracy of the control system in which the sensor is used. Therefore, it is important to improve the strength and stability of the contact to thereby minimize an increase in the internal resistance of the sensor element during actual operations.

To enhance the strength of the contact of the gas sensitive thick film, JP-A 60-93949 proposes to intentionally produce minute undulations in the ceramic substrate surface before forming the thick film by applying ceramic grains to the substrate surface. However, even if this measure is taken, the tightness of contact of the thick film with the underlying electrode films is still insufficient in a microscopical sense, so that the internal resistance between the thick film and the electrode films is liable to deviate from a standard value. Besides, there is another cause of an increase in the internal resistance and resultant deterioration of the gas sensing performance during use of the gas sensor element. That is, impurities contained in the substrate and/or the thick film migrate to accumulate in the micropores of the thick film in the region adjacent the interface between the thick film and each of the underlying electrode films.

Concerning the problem of the increase in the aforementioned internal resistance, we recognized that because of the contact of the gas sensitive thick film and the electrode films in a plane there occurs concentration of an interfacial tension in the directions parallel to the plane, and that due to the concentration of the interfacial tension the tightness of contact between the thick film and each electrode film becomes worse as time elapses with a resultant increase in the contact resistance.

JP-A 62-5165 (Jan. 12, 1987) proposes to interpose a conductor between the gas sensitive porous thick film and each of the underlying electrode films by depositing platinum or an alloy or mixture of platinum with another noble metal. The deposition of the noble metal is accomplished by impregnating the porous thick film with a solution of a nobel metal compound and then making a heat treatment in hydrogen gas at about 700° C. By the deposition of the noble metal conductor at the interface between the thick film and each electrode film, the manner of contact between the thick film and each electrode film changes from two-dimensional contact to three-dimensional contact. Therefore, the strength of contact augments and the concentration of tension in the directions parallel to the interface is relieved, and consequently the contact resistance is stabilized. However, it has been revealed that the manner of the deposition of the noble metal is greatly influenced by the conditions of the heat treatment in a reducing gas atmosphere. In this regard we have already proposed in JP-A 63-231255 (Sep. 27, 1988) to carry out the heat treatment of the thick film impregnated with a solution of a platinum compound in hydrogen gas at a temperature in the range from 60° to 180° C. After that we have reached the present invention by finding still better conditions of the heat treatment for establishing very good and stable contact between the thick film and the electrode films.

SUMMARY OF THE INVENTION

It is an object of the present invention to provide a method of producing a thick film gas sensor element in which the contact between the gas sensitive thick film and the underlying electrode films are improved in strength, uniformity and stability by the deposition of a noble metal conductor at the interface between the thick film and each electrode film.

The present invention provides a method of producing a thick film gas sensor element, the method comprising the steps of forming at least one pair of electrode films on a surface of a ceramic substrate by using at least one metal of the platinum group as the principal material of the electrode films, applying a paste comprising a powder of a gas sensitive material to the surface of the ceramic substrate so as to cover selected portions of the electrode films together with a selected area of the substrate surface and firing the applied paste to thereby form a porous thick film of the gas sensitive material, impregnating the porous thick film with a solution of at least one compound of a metal of the platinum group and thereafter maintaining the substrate in a reducing gas, which contains a controlled amount of vapor of water such that the relative humidity in the reducing gas is in the range from 5 to 90%, at a temperature in the range from 10° C. to 135° C. to thereby deposit a conductor comprising at least one metal of the platinum group at the interface between the thick film and each of the electrode films.

In a gas sensor element to be produced by a method according to the invention, the principal component of the gas sensitive material is usually a transition metal oxide which exhibits a change in its electrical resistance with a change in the concentration of a specific gas in an environmental gas atmosphere. For example, $SnO_2$, $ZnO$ or $Fe_2O_3$ is used in a propane gas sensor or a humidity sensor, and $TiO_2$ or $CoO$ is used in an oxygen sensor.

The electrode films are usually formed by a thick film technique using a paste containing a powder of the electrode material. In thick film gas sensor elements for use at high temperatures the electrode material is usually platinum or an alloy or mixture of platinum and another metal of the platinum group such as rhodium or palladium. As the conductor to be deposited at the interface between the gas sensitive thick film and each electrode film, it is suitable to employ the noble metal(s) used as the electrode material.

In the method according to the invention, after impregnating the gas sensitive thick film with a solution of a noble metal compound the treatment of the sensor element in a reducing gas is performed by introducing a controlled amount of vapor of water into the reducing gas and controlling the humidity in the reducing gas within the range from 5 to 90% in terms of relative humidity and correlatively to the treating temperature which should be in the range from 10° C. to 135° C. According to JP-A 62-5165 and JP-A 63-231255, a heat treatment for fundamentally the same purpose is carried out in dry hydrogen gas in which humidity is practically 0%. In contrast, according to the invention a controlled amount of moisture is intentionally introduced into hydrogen gas or an alternative reducing gas. This is an important feature of the present invention.

As the reducing gas it is suitable to use hydrogen gas, carbon monoxide gas or methane gas, or a mixture of at least two of these three kinds of reducing gases. If desired the reducing gas may be diluted with an inactive gas such as nitrogen, argon gas or carbon dioxide gas.

Optionally, the treatment in a reducing gas atmosphere may be followed by a heat treatment at a temperature above about 150° C., preferably above 200° C., in the air, a reducing gas such as hydrogen or an inactive gas such as nitrogen. This heat treatment is effective for completely decomposing the noble metal compound(s) possibly remaining in the gas sensitive thick film and/or at the aforementioned interface and consequently for further stabilizing the deposited noble metal conductor.

By the method according to the invention a noble metal conductor such as platinum deposits at the interface between the gas sensitive porous thick film and each of the underlying electrode films with good uniformity of dispersion in the interface. In the obtained gas sensor element the noble metal conductor interposes between the gas sensitive thick film and each electrode film, so that the contact between the two films surely becomes three-dimensional. Therefore, the contact is reinforced and stabilized, and the internal resistance of the gas sensor element does not seriously deviate from a standard value and does not seriously change during use of the sensor element.

The noble metal conductor deposits not only at the aforementioned interface but also in the gas sensitive porous thick film in the region adjacent the interface to fill the micropores in that region. The deposition of the conductor in the micropores near the interface is effective for preventing impurities from migrating into and accumulating in these pores to cause an increase in the internal resistance of the sensor element as an aging phenomenon.

Thus, the method according to the invention serves the purpose of producing a thick film gas sensor element improved in the stability of its function and also in durability, and by this method such an improved sensor element can be produced stably and efficiently.

BRIEF DESCRIPTION OF THE DRAWINGS

FIGS. 1, 3, 5, 7, 9 and 11 are plan views of an unfired ceramic substrate under processing for producing a thick film gas sensor element and illustrate the sequential steps of a method according to the invention;

FIGS. 2, 4, 6, 8, 10 and 12 are cross-sectional or end elevational views of the unfired ceramic substrate corresponding to FIGS. 1, 3, 5, 7, 9 and 11, respectively;

DESCRIPTION OF THE PREFERRED EMBODIMENTS

Figure 13:
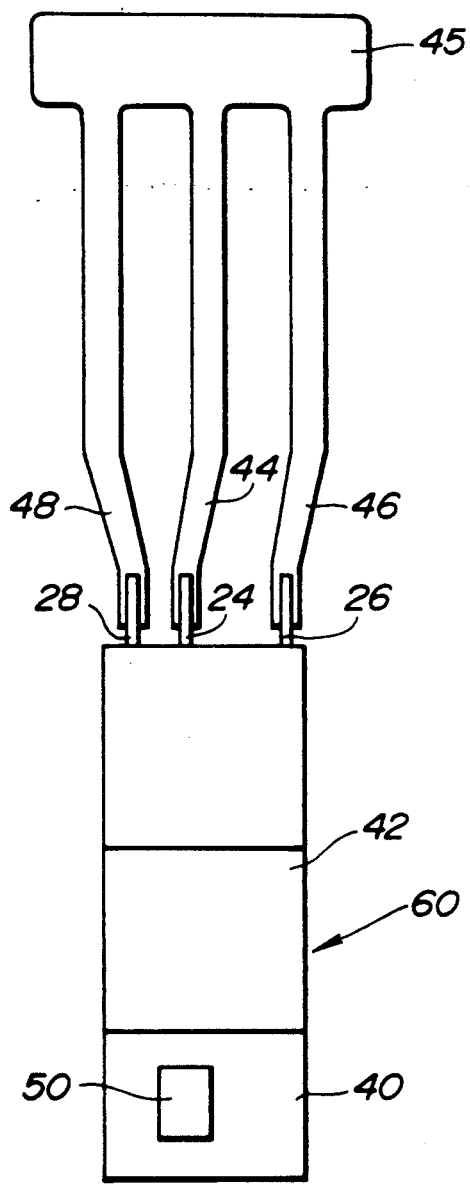
FIG. 13 is a plan view of the thick film gas sensor element and shows the manner of connecting electrical terminals to the sensor element.

As an embodiment of the invention, a thick film gas sensor element is produced by the following process. The gas sensor element has a sintered ceramic substrate which is provided with a pair of electrodes and a resistance heater element. The principal material of the substrate is a ceramic material high in heat resistance such as, for example, alumina, mullite, steatite or forsterite. FIGS. 1 to 10 illustrate the process of preparing the ceramic substrate, and FIGS. 11 and 12 illustrate the formation of a thick film of a gas sensitive substance on the ceramic substrate.

In FIG. 1 numeral 10 indicates a green sheet which turns into a ceramic plate by firing. This green sheet 10 is formed so as to provide a main part of the ceramic substrate of the gas sensor element. FIG. 2 is a sectional view taken along the line 2—2 in FIG. 1. On the upper surface of the green sheet 10, first and second electrode patterns 12 and 14 are formed by a thick film printing method using a conductive paste such as a platinum paste. Besides, a heater pattern 16 is formed by the same method so as to join with the second electrode pattern 14 in a terminal section, and terminal patterns 18, 20 and 22 are supplemented to the electrode and heater patterns.

As shown in FIGS. 3 and 4, lead wires 24, 26 and 28 are attached to the terminal patterns 18, 20, and 22, respectively.

Referring to FIG. 5, another green sheet 30 is placed on the green sheet 10. The two green sheets 10 and 30 have the same width and the same length so that the printed patterns on the surface of the green sheet 10 are all covered by the green sheet 30. However, in advance the green sheet 30 is formed with a window-like opening 32 such that tip portions of the two electrode patterns 12, 14 are exposed in this opening 32. FIG. 6 is a sectional view taken along the line 6—6 in FIG. 5. The green sheet 30 is tightly bonded to the green sheet 10 by application of heat and pressure.

Referring to FIGS. 7 and 8, a green sheet 36 shorter than the green sheets 10 and 30 is placed on and bonded to the green sheet 30 by application of heat and pressure. Furthermore, as shown in FIGS. 9 and 10, a still shorter green sheet 38 is placed on and bonded to the green sheet 36 by application of heat and pressure. As the result the major part of the green sheet 30 is covered stepwise by the two green sheets 36 and 38, but the opening 32 is left exposed. These green sheets 36 and 38 are added for the purpose of reinforcing the ceramic substrate.

In the state shown in FIG. 9, it is preferred to apply ceramic grains to the exposed surface of the green sheet 30 and the surface of the green sheet 10 exposed in the opening 32 for the purpose of providing minute undulations to the mentioned surfaces. The material of the ceramic grains is similar to the ceramic material of the green sheets. For example, the ceramic grains are about 100 μm in diameter.

After that the laminate in FIG. 9 is fired at a temperature suitable for sintering of the employed ceramic material.

Referring to FIG. 11 and FIG. 12 which is a sectional view taken along the line 12—12 in FIG. 11, by the above firing operation the initially laminated green sheets 10 and 30 turn into a ceramic substrate 40 while the overlying green sheets 36 and 38 turn into a ceramic cover layer 42 which is tightly and unitarily adhering to the ceramic substrate 40. The opening 32 in the green sheet 30 becomes a recess in the ceramic substrate 40. In the ceramic substrate 40 the electrode patterns 12 and 14 have turned into metallic electrode films and the heater pattern 18 into a metallic resistor film.

Next, a porous thick film 50 of a gas sensitive material is formed so as to entirely and tightly cover the substrate surface and the tip portions of the electrodes 12, 14 exposed in the recess 32. To form the thick film 50 a paste containing a powder of the gas sensitive material is applied to the ceramic substrate 40 to fill the recess 32 with the paste. The method of applying the paste to fill the recess 32 can be chosen from ordinary methods such as thick film printing method, dropping or dripping method, etc. The applied paste may heap above the upper surface of the substrate 40 as shown in FIG. 12. By firing the paste on the substrate under suitable conditions, which depend on the kind of the gas sensitive material, the paste film turns into a solid and porous thick-film 50 of the gas sensitive substance.

By the above operations a thick film gas sensor element 60 is seemingly completed. However, according to the invention it is essential to subsequently perform the following operations.

The porous thick film 50 is treated with a solution of at least one kind of platinum group metal compound, which decomposes under reducing conditions to deposit the platinum group metal, such that the solution permeates into the thick-film 50. It is suitable to employ a compound of the platinum group metal used as the material of the electrodes 12, 14. Usually an aqueous solution is used, and the thick film 50 impregnated with the solution is dried at a temperature not higher than 150° C. to remove a large portion of water from the solution. The drying is not an essential operation, but this is favorable for the efficiency of the subsequent operation.

Next, the nearly finished gas sensor element 60 is maintained in a reducing gas atmosphere of a controlled humidity at a temperature chosen within the range from 10° C. to 350° C. to accomplish decomposition of the platinum group metal compound(s) in the thick film 50 and resultant deposition of the platinum group metal(s) at the interface between the thick film 50 and each of the electrode films 12 and 14. The humidity in the reducing gas atmosphere is controlled within the range from 5 to 90% in terms of relative humidity. Since the electrodes 12, 14 made of the platinum group metal provide nuclei of deposition of the metal, deposition of the metal(s) from the decomposed compound(s) occurs preferentially on the surfaces of the electrode films 12, 14 and in the micro-pores of the thick film 50 in a region adjacent the electrode surfaces. The temperature of the reducing gas atmosphere and the humidity in the gas atmosphere are correlatively chosen such that the temperature and the humidity, in terms of relative humidity, fall in the Region A in the chart of FIG. 16, and preferably in the narrower Region B.

After the treatment in the reducing gas atmosphere for the deposition of the platinum group metal(s), it is optional to heat the gas sensor element to a temperature of 150° C. or above in either the air or a reducing gas atmosphere for decomposing the platinum group metal compound(s) possibly remaining undecomposed and stabilizing the deposited platinum group metal(s).

EXAMPLE 1

A thick-film oxygen sensor element of the construction shown in FIG. 11 was produced by the process described above with reference to FIGS. 1 to 12.

The principal material of the green sheets 10, 30, 36 and 38 was a mixture of 92 wt % $Al_2O_3$ powder, 4 wt % of $SiO_2$ powder, 2 wt % of CaO powder and 2 wt % of MgO powder. Every powder had a mean particle size of 1.5 μm. A slurry was prepared by mixing 100 parts by weight of this powder mixture with 12 parts by weight of a polyvinyl butyral resin and 6 parts by weight of dibutylphthalate in an organic solvent, and the slurry was used to form each green sheet by a doctor blade method. The green sheet 10 had a thickness of 1 mm, and the green sheet 30 had a thickness of 0.8 mm.

The electrode patterns 12, 14, the heater pattern 16 and the terminal patterns 18, 20, 22 were formed by using a paste containing Pt powder and $Al_2O_3$ powder amounting to 7 wt % of the Pt powder. The lead wires 24, 26, 28 were platinum wires having a diameter of 0.2 mm.

The firing of the laminated green sheets in the state of FIG. 9 was performed in the air at 1500° C. for 2 hr.

The porous thick film 50 was formed by using a paste prepared by mixing 100 parts by weight of $TiO_2$ powder having a mean particle size of 1.2 μm and 3 parts by weight of ethyl cellulose in 2-(2-butoxyethoxy)ethyl alcohol to adjust the viscosity of the mixture to 300 poises. The firing of the $TiO_2$ paste (50) applied to the substrate 40 was performed in the air at 1200° C. for 1 hr.

A number of samples of the oxygen sensor element (60) were produced by the same method and under the same conditions, and the porous thick film 50 of $TiO_2$ in each sample was impregnated with an aqueous solution of chloroplatinic acid (200 g/l) by dropping 2 μl of the solution to the thick film 50. For only one sample the chloroplatinic acid solution was modified by adding rhodium chloride such that the weight ratio of Pt to Rh contained in the solution became 90:10. After that each sample was maintained in hydrogen gas containing moisture for 60 min, except two samples which were maintained in the same gas atmosphere only for 10 min and for 5 min, respectively. The temperature of the hydrogen gas atmosphere and relative humidity in the gas atmosphere were variously set as shown in Table 1.

Figure 14:
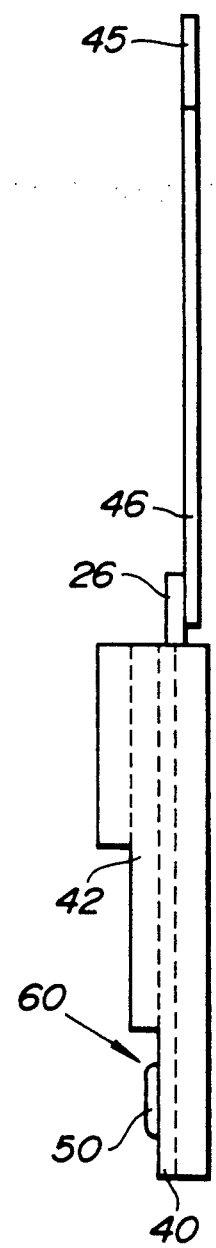
FIG. 14 is a side elevational view of the gas sensor element in FIG. 13.

After the above treatment, electrical terminals were connected to each oxygen sensor element sample (60). Referring to FIGS. 13 and 14, a terminal member having three terminals 44, 46, 48 and a common runner part 45 was formed by etching a nickel sheet having a thickness of 0.3 mm, and the three terminals 44, 46 and 48 were welded to the platinum lead wires 24, 26 and 28 of the oxygen sensor element 60, respectively. (The runner part 45 was removed before installing the sensor element 60 in an oxygen sensor.)

Figure 15:
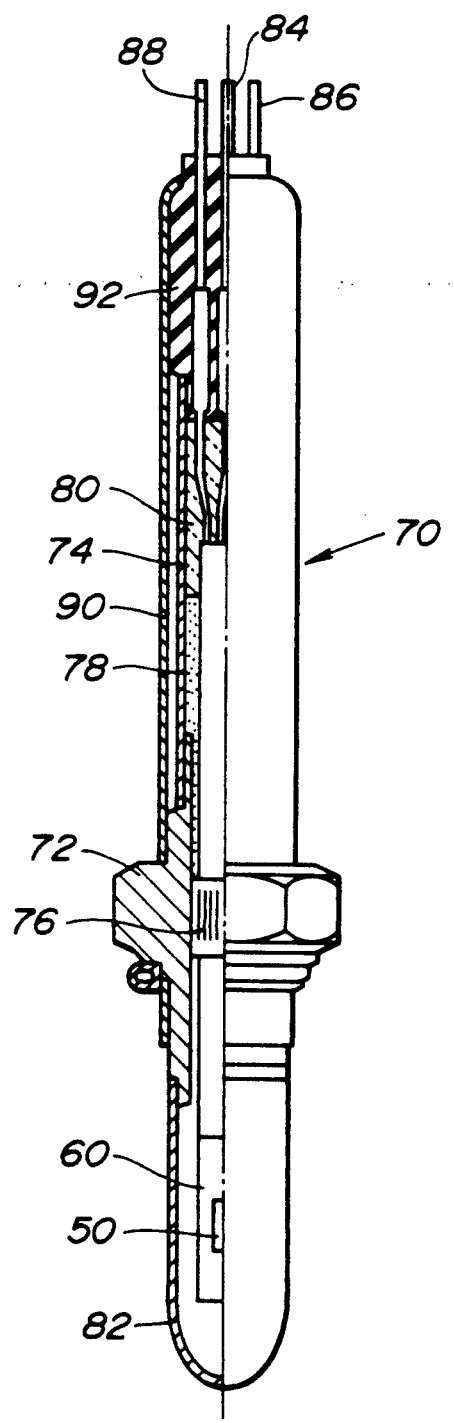
FIG. 15 is partly cutaway plan view of a gas sensor using the thick film gas sensor element shown in FIGS. 13 and 14.

After that each oxygen sensor element sample was installed in an oxygen sensor for use in the exhaust system of an internal combustion engine. FIG. 15 shows this oxygen sensor at 70. The oxygen sensor 70 has a metal shell 72 for attachment to the exhaust manifold or exhaust pipe of the engine, an inner tube 74 for holding the oxygen sensor element 60 and an outer tube 90 for protecting the inner tube 74. Using a supportive spacer 76 the terminals of the sensor element 60 extend through the inner tube 74, and the space in the inner tube 74 is filled with a packed insulating powder 78 (for example, 1:1 mixture of talc and glass powder) and a glass seal 80 using a low melting point glass. The main part of the sensor element 60 is encapsulated by a protective cap 82 fixed to the shell 72. The cap 82 is permeable to gases or is formed with openings. The terminals of the sensor element 60 are connected to lead wires 84, 86, 88, respectively. An end portion of the outer tube 90 is filled with a silicone rubber sealant 92 for insulating and protecting the connections of the lead wires to the sensor element terminals.

In operating the oxygen sensor 70 the resistance heater (16) in the sensor element 60 is energized by using the lead wires 86 and 88 to keep the oxygen sensitive thick film 50 heated and active. The concentration of oxygen in a gas which makes contact with the $TiO_2$ film 50 is detected by measuring a change in the resistance of the film 50 by using the lead wires 84 and 86.

The internal resistance of the sensor element sample 60 in each oxygen sensor 70 was measured in a propane burner which was operated with an excess air factor ($\lambda$) of 0.9. The combustion gas temperature was 350° C. In measuring the internal resistance, a voltage of +12 V was applied to the lead wire 88 (connected to the heater in the sensor element 60) while the lead wire 86 was grounded, and a fixed resistance of 50 k$\Omega$ was connected between the lead wires 84 and 86. After that, each oxygen sensor 70 was subjected to an endurance test, which was heating the oxygen sensor for 5 min in a 900° C. flame of a Bunsen burner and immediately cooling for 5 min and cycling the heating-and-cooling 500 times. The application of the voltage of +12 V and the connection of the resistance of 50 k$\Omega$ were maintained during the endurance test. After the endurance test the internal resistance of the sensor element sample 60 in the oxygen sensor was measured. The results are shown in Table 1.

TABLE 1

| Sample No. | Treatment | | Internal Resistance | |
| --- | --- | --- | --- | --- |
| | Temperature (°C.) | Relative Humidity (%) | Initially (k$\Omega$) | After Endurance Test (k$\Omega$) |
| 1 | 50 | 100 | 1.4 | 8.0 |
| 2 | 60 | 100 | 1.2 | 2.9 |
| 3 | 180 | 100 | 1.9 | 2.5 |
| 4 | 200 | 100 | 1.8 | 6.2 |
| 5 | 10 | 90 | 1.5 | 7.2 |
| 6 | 20 | 90 | 1.1 | 2.4 |
| 7 | 30 | 90 | 1.0 | 2.2 |
| 8 | 50 | 90 | 1.0 | 2.0 |
| 9 | 70 | 90 | 1.1 | 2.0 |
| 10 | 90 | 90 | 1.0 | 2.0 |
| 11 | 110 | 90 | 1.0 | 2.0 |
| 12 | 130 | 90 | 1.1 | 2.4 |
| 13 | 160 | 90 | 1.2 | 2.5 |
| 14 | 180 | 90 | 1.4 | 7.1 |
| 15 | 10 | 80 | 1.5 | 2.5 |

TABLE 1-continued

| Sample No. | Treatment | | Internal Resistance | |
| --- | --- | --- | --- | --- |
| | Temperature (°C.) | Relative Humidity (%) | Initially (k$\Omega$) | After Endurance Test (k$\Omega$) |
| 16 | 30 | 80 | 1.1 | 2.0 |
| 17 | 70 | 80 | 1.1 | 1.5 |
| 18 | 130 | 80 | 1.2 | 2.0 |
| 19 | 150 | 80 | 1.1 | 2.3 |
| 20 | −5 | 70 | 1.5 | 7.8 |
| 21 | 5 | 70 | 1.3 | 2.1 |
| 22 | 10 | 70 | 1.1 | 2.0 |
| 23 | 30 | 70 | 0.9 | 1.0 |
| 24 | 70 | 70 | 1.0 | 1.4 |
| 25 | 110 | 70 | 1.1 | 1.7 |
| 26 | 135 | 70 | 1.1 | 1.8 |
| 27 | 140 | 70 | 1.2 | 2.5 |
| 28 | 150 | 70 | 1.6 | 7.4 |
| 29 | 10 | 60 | 0.9 | 1.0 |
| 30 | 30 | 60 | 0.9 | 1.0 |
| 31 | 70 | 60 | 1.0 | 1.4 |
| 32 | 110 | 60 | 1.2 | 1.8 |
| 33 | 130 | 60 | 1.1 | 2.0 |
| 34 | 10 | 50 | 0.8 | 0.9 |
| 35 | 30 | 50 | 0.9 | 0.9 |
| 36 | 110 | 50 | 1.2 | 1.9 |
| 37 | 130 | 50 | 1.2 | 2.7 |
| 38 | −50 | 40 | 2.0 | 9.0 |
| 39 | −15 | 40 | 1.6 | 7.7 |
| 40 | −5 | 40 | 1.3 | 2.4 |
| 41 | 10 | 40 | 0.8 | 0.9 |
| 42 | 30 | 40 | 0.9 | 1.0 |
| 43 | 40 | 40 | 1.0 | 2.0 |
| 44 | 70 | 40 | 1.1 | 2.0 |
| 45 | 90 | 40 | 1.0 | 2.0 |
| 46 | 115 | 40 | 1.2 | 2.5 |
| 47 | 130 | 40 | 1.5 | 7.2 |
| 48 | 200 | 40 | 1.9 | 8.5 |
| 49 *1 | 40 | 40 | 1.1 | 1.6 |
| 50 *2 | 40 | 40 | 1.2 | 2.4 |
| 51 *3 | 40 | 40 | 1.0 | 1.7 |
| 52 *4 | 40 | 40 | 0.9 | 1.7 |
| 53 *5 | 40 | 40 | 1.1 | 1.9 |
| 54 | 10 | 30 | 0.7 | 0.8 |
| 55 | 30 | 30 | 0.9 | 0.9 |
| 56 | 50 | 30 | 0.9 | 1.0 |
| 57 | 90 | 30 | 1.2 | 1.8 |
| 58 | −5 | 20 | 1.4 | 2.4 |
| 59 | 10 | 20 | 0.9 | 1.0 |
| 60 | 30 | 20 | 0.8 | 1.0 |
| 61 | 50 | 20 | 0.8 | 1.0 |
| 62 | 90 | 20 | 1.2 | 2.0 |
| 63 | 100 | 20 | 1.4 | 2.5 |
| 64 | 10 | 10 | 0.8 | 1.0 |
| 65 | 30 | 10 | 0.9 | 1.0 |
| 66 | 50 | 10 | 0.9 | 1.0 |
| 67 | 70 | 10 | 1.0 | 1.4 |
| 68 | 90 | 10 | 1.4 | 1.9 |
| 69 | 10 | 5 | 1.2 | 1.9 |
| 70 | 30 | 5 | 1.1 | 1.4 |
| 71 | 50 | 5 | 1.1 | 1.3 |
| 72 | 70 | 5 | 1.4 | 1.5 |
| 73 | 90 | 5 | 1.5 | 2.0 |
| 74 | −15 | 0 | 1.6 | 7.9 |
| 75 | −5 | 0 | 1.2 | 2.2 |
| 76 | 10 | 0 | 1.3 | 2.1 |
| 77 | 30 | 0 | 1.5 | 2.1 |
| 78 | 50 | 0 | 1.4 | 2.2 |
| 79 | 70 | 0 | 1.5 | 2.1 |
| 80 | 95 | 0 | 1.3 | 2.1 |
| 81 | 120 | 0 | 1.5 | 8.1 |

Notes
*1: Sample No. 49 was treated only for 10 min.
*2: Sample No. 50 was treated only for 5 min.
*3: Sample No. 51 was subsequently heated in $H_2$ at 700° C. for 2 hr.
*4: Sample No. 52 was subsequently heated in the air at 700° C. for 2 hr.
*5: Sample No. 53 was produced by impregnating the thick film (50) with the mixed solution of chloroplatinic acid and rhodium chloride.

Figure 16:
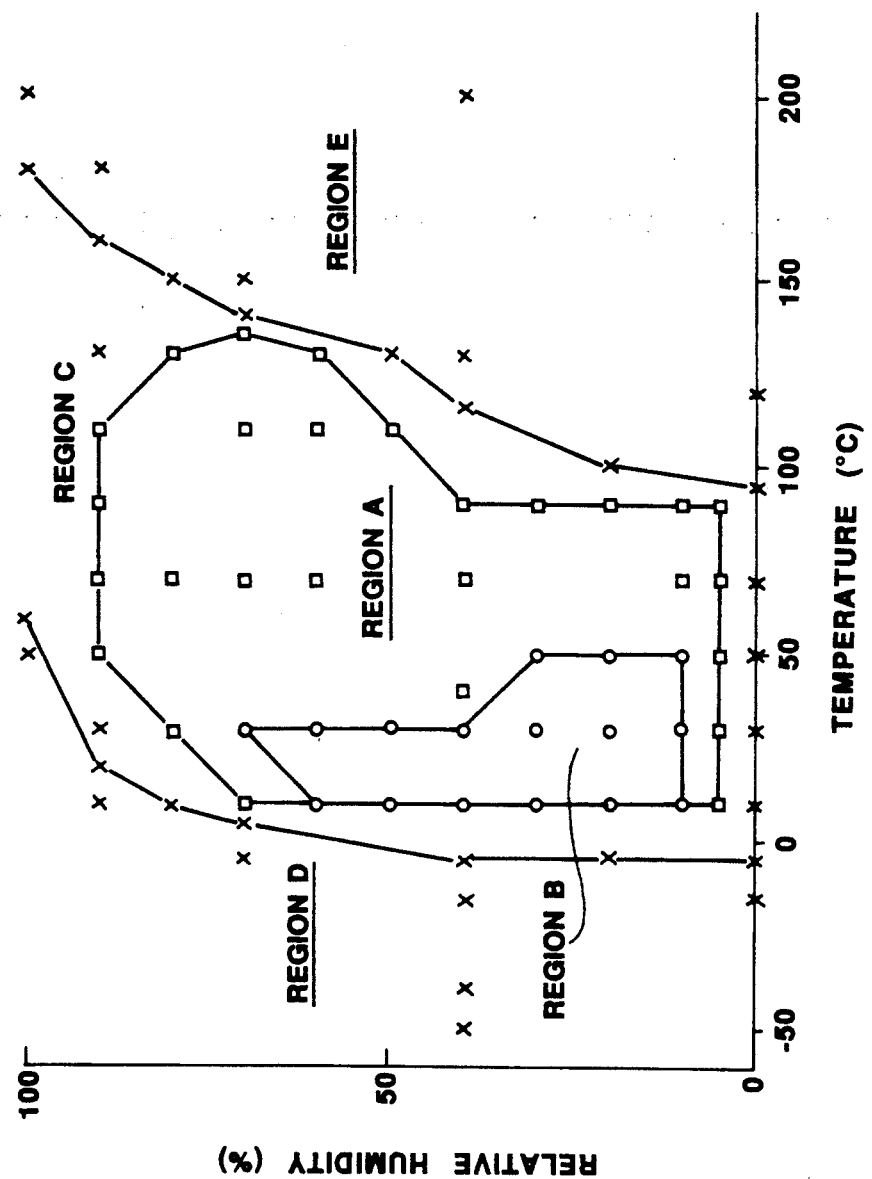
FIG. 16 is a chart showing suitable and unsuitable temperature and humidity conditions of the treatment of an unfinished thick film gas sensor element in a reducing gas atmosphere in producing the gas sensor element by a method according to the invention.

As can be seen in Table 1, after the endurance test some samples exhibited a considerable increase in the internal resistance, which is indicative of a deterioration of the contact of the TiO₂ thick film 50 with the electrodes 12, 14 and, hence, insufficiency of the deposition of platinum at the interface between the thick film and each electrode or inferiority of the manner of deposition of platinum. We judged that the deposition of platinum and the stability of the contact between the thick film and the electrodes were quite satisfactory when the internal resistance measured after the endurance test did not exceed 2 kΩ. By this criterion, the relations between the results of the endurance test and the temperature-humidity conditions of the treatment of the TiO₂ thick film impregmated with the platinum compound in hydrogen gas atmosphere were as shown in FIG. 16. In FIG. 16: the square marks (□) represent the samples not higher than 2 kΩ in internal resistance but higher than 1 kΩ; the cross marks (X) represent the samples higher than 2 kΩ in internal resistance; and the circle marks (○) the samples not higher than 1 kΩ internal resistance.

In FIG. 16 it is seen that when the temperature-humidity conditions of the treatment are in the Region A the obtained sensor element 60 is good in stability of internal resistance.

In FIG. 16 the Region A is a closed region defined by consecutive line segments starting at the point (square mark) designated by the coordinates (10° C., 5% RH) and returning to this point via the following points (square marks) in the recited order: (10° C., 70% RH), (30° C., 80% RH), (50° C., 90% RH), (110° C., 90% RH), (130° C., 80% RH), (135° C., 70% RH), (130° C., 60% RH), (110° C., 50% RH), (90° C., 40% RH) and (90° C., 5% RH).

In this Region A the deposition of platinum by the action of the reducing gas proceeds smoothly, and platinum deposits finely and densely at the interface between the thick film 50 and each electrode 12, 14 with the effect of enhancing the connection of the thick film 50 to each electrode 12, 14 both mechanically and electrically. In the Region B which is a limited area of the Region A, the stability of the internal resistance becomes still better.

In FIG. 16 the region B is a closed region defined by consecutive line segments starting at the point (circle mark) designated by the coordinates (10° C., 10% RH) and returning to this point via the following points (circle marks) in the recited order: (10° C., 60% RH), (30° C., 70% RH), (30° C., 40% RH), (50° C., 30% RH) and (50° C., 10% RH).

In the Region C surrounding the Region A, the stability of the internal resistance is tolerably good but is not fully satisfactory. That is, in the Region C the internal resistance of the sensor element subjected to the endurance test was higher than 2 kΩ but not higher than 5 kΩ. In the Region D on the lower temperature side and also in the Region E on the higher temperature side, the internal resistance after the endurance test became higher than 5 kΩ. In the Region D the rate of deposition of platinum is low and the amount of deposition of platinum is insufficient. In the Region E, the amount of deposition of platinum at the interface between the thick-film 50 and each electrode 12, 14 is insufficient probably by reason that the rate of decomposition of chloroplatinic acid in the thick film 50 is too high compared with the rate of its migration to the interface between the film 50 and each electrode 12, 14, so that a large portion of deposited platinum is finely dispersed in the thick film 50.

EXAMPLE 2

The sensor element manufacturing process of Example 1 was repeated until the step of impregnating the porous thick film 50 of TiO₂ with the chloroplatinic acid solution. Several samples of the sensor element (60) were produced under the same conditions.

After that each sample was maintained in a reducing gas, which was variously chosen as shown in Table 2. In every case the temperature of the reducing gas was 40° C., and relative humidity in the reducing gas was 40%, and the sample was maintained in the reducing gas for 60 min. Before and after the treatment with the reducing gas the internal resistance of each sample was measured by the same method as in Example 1. The results are shown in Table 2.

TABLE 2

| | Internal Resistance | |
|---|---|---|
| Reducing Gas (vol %) | Initially (kΩ) | After Endurance Test (kΩ) |
| CO | 1.0 | 1.9 |
| CO(50%)/H₂(50%) | 1.0 | 1.7 |
| CO(50%)/N₂(50%) | 1.3 | 1.9 |
| CH₄ | 1.2 | 1.5 |
| CH₄(50%)/H₂(50%) | 1.0 | 1.5 |
| CH₄(50%)/N₂(50%) | 1.2 | 2.0 |
| H₂(50%)/N₂(50%) | 0.8 | 1.6 |
| H₂(30%)/N₂(97%) | 1.1 | 1.7 |
| H₂(1%)/N₂(99%) | 1.1 | 2.5 |
| H₂(50%)/CO₂(50%) | 0.9 | 1.7 |
| H₂(50%)/Ar(50%) | 0.9 | 1.7 |

What is claimed is:

1. A method of producing a thick film gas sensor element, comprising the steps of:
   (a) forming at least one pair of electrode films on a surface of a ceramic substrate wherein at least one metal selected from the group consisting of the platinum group of the periodic chart is the principal material of the electrode films;
   (b) applying a paste comprising a powder of a gas sensitive material to said surface of the ceramic substrate so as to cover selected portions of the electrode films together with a selected area of said surface and firing the applied paste to thereby form a porous thick film of the gas sensitive material;
   (c) impregnating said porous thick film with a solution of at least one compound of a metal selected from the group consisting of the platinum group of the periodic chart; and
   (d) after step (c), maintaining the substrate in a reducing gas, which includes a controlled amount of water vapor such that the relative humidity in the reducing gas and the temperature in said reducing gas are within the region A indicated in FIG. 16 of the accompanying drawings to thereby deposit a conductor comprising at least one metal of the platinum group at the interface between said porous thick film and each of the electrode films.

2. A method according to claim 1, wherein said principal material of the electrode films comprises platinum and said solution comprises a platinum compound.

3. A method according to claim 2, wherein said platinum compound is chloroplatinic acid.

4. A method according to claim 2, where in said solution further comprises a compound of another metal selected from the group consisting of rhodium and palladium.

5. A method according to claim 1, wherein said solution is an aqueous solution.

6. A method according to claim 1, wherein said temperature at step (d) and the relative humidity in said reducing gas are within the Region B indicated in the chart of FIG. 16 of the accompanying drawings.

7. A method according to claim 1, wherein said reducing gas is selected from the group consisting of hydrogen gas, carbon monoxide gas and methane gas.

8. A method according to claim 1, wherein said reducing gas is diluted with an inactive gas.

9. A method according to claim 8, wherein said inactive gas is selected from the group consisting of nitrogen gas, argon gas and carbon dioxide gas.

10. A method according to claim 1, further comprising, after step (d), a step of heating the gas sensor element at a temperature not lower than 150° C.

11. A method according to claim 10, wherein the heating after step (d) is carried out at a temperature higher than 200° C.

12. A method according to claim 1, wherein said gas sensitive material is a transition metal oxide selected from the group consisting of $SnO_2$, $ZnO$, $Fe_2O_3$, $TiO_2$ and $CoO$.

13. A method according to claim 7, wherein the reducing gas has a temperature of 10° C. to 50° C. and a relative humidity of 10% to 70%.

14. A method of producing a thick film gas sensor element, comprising the steps of:

(a) forming at least one pair of electrode films on a surface of a ceramic substrate wherein at least one metal selected from the group consisting of the platinum group of the periodic chart is the principal material of the electrode films;

(b) applying a paste comprising a powder of a gas sensitive material to said surface of the ceramic substrate so as to cover selected portions of the electrode films together with a selected area of said surface and firing the applied paste to thereby form a porous thick film of the gas sensitive material;

(c) impregnating said porous thick film with a solution of at least one compound of a metal selected from the group consisting of the platinum group of the periodic chart; and (d) after step (c), maintaining the substrate in a reducing gas, which includes a controlled amount of water vapor such that the relative humidity in the reducing gas and the temperature in said reducing gas falls within an area on a x vs. y plot of relative humidity (RH) vs. temperature (°C.) defined by consecutive line segments connecting the following coordinates in order: (10° C., 5% RH); (10° C., 70% RH); (30° C., 80% RH); (50° C., 90% RH); (110° C., 90% RH); (130° C., 80% RH); (135° C., 70% RH); (130° C., 60% RH); (110° C., 50% RH); (90° C., 40% RH); (90° C., 5% RH); and back to (10° C., 5% RH), to thereby deposit a conductor comprising at least one metal of the platinum group at the interface between said porous thick film and each of the electrode films.

15. A method according to claim 14, wherein the relative humidity and temperature utilized in step (d) falls within an area of x vs. y plot of relative humidity (RH) vs. temperature (°C.) defined by consecutive line segments connecting the following coordinates in order: (10° C., 10% RH); (10° C., 60% RH); (30° C., 70% RH); (30° C., 40% RH); (50° C., 30% RH); (50° C., 10% RH); and back to (10° C., 10% RH).

* * * * *